United States Patent [19]

Rogoff

[11] Patent Number: 4,538,616

[45] Date of Patent: Sep. 3, 1985

[54] BLOOD SUGAR LEVEL SENSING AND MONITORING TRANSDUCER

[76] Inventor: Robert Rogoff, 223 Louella La., Nokomis, Fla. 33555

[21] Appl. No.: 517,065

[22] Filed: Jul. 25, 1983

[51] Int. Cl.³ .......................... A61B 5/00; A61M 1/03
[52] U.S. Cl. ........................................ 128/632; 604/66
[58] Field of Search .............. 128/632, 635, 637, 675, 128/748; 204/403, 415; 604/50, 66, 67; 320/46

[56] References Cited

U.S. PATENT DOCUMENTS

| | | | |
|---|---|---|---|
| 3,243,682 | 3/1966 | Gold | 320/46 |
| 3,818,765 | 6/1974 | Eriksen | 128/675 |
| 3,982,535 | 9/1976 | Balarton | 604/67 |
| 4,275,739 | 6/1981 | Fischell | 128/419 PS |

Primary Examiner—Lee S. Cohen
Assistant Examiner—Steven Falk
Attorney, Agent, or Firm—Hauke and Patalidis

[57] ABSTRACT

A sensing and monitoring transducer for detecting blood sugar levels of a person, the transducer being in the form of a miniature enclosure implanted in the person's bloodstream. The enclosure has a chamber, filled with a standard osmostic solution, closed on one side by an osmostic semi-permeable membrane and at another end by a flexible impermeable diaphragm carrying an electrical contact. Transfer of fluid from the chamber containing the standard osmostic solutions through the semi-permeable membrane as a function of variations in blood sugar level causes the flexible diaphragm to be deflected in one direction or the other for placing the electric contact carried by the diaphragm in engagement with one or the other of a pair of fixed electrical contacts, such as to remotely operate appropriate peripheral equipment such as low and high blood sugar level alarms, or insulin and glucose pumps injecting respectively a dosage of insulin and of a glucose solution in the person's bloodstream to maintain the blood sugar level within acceptable limits.

9 Claims, 3 Drawing Figures

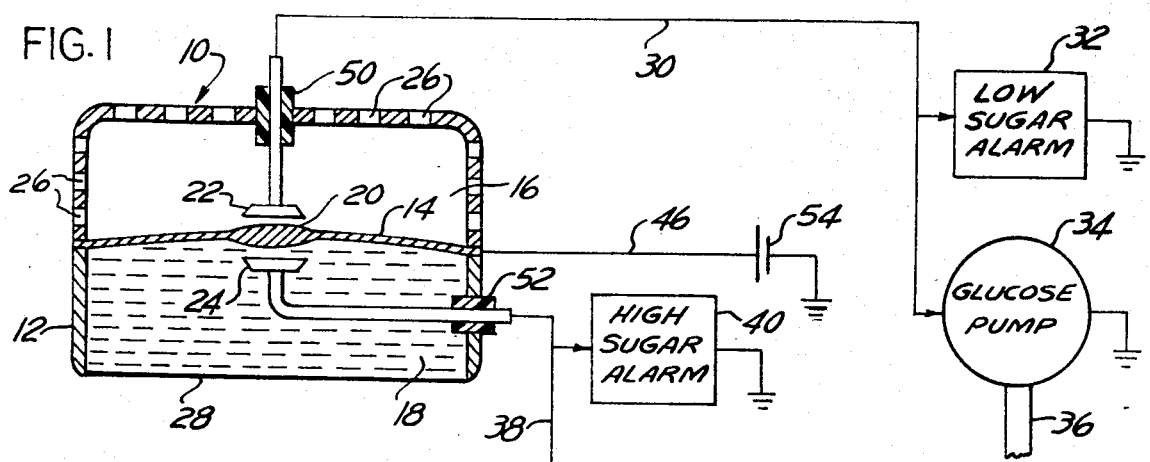
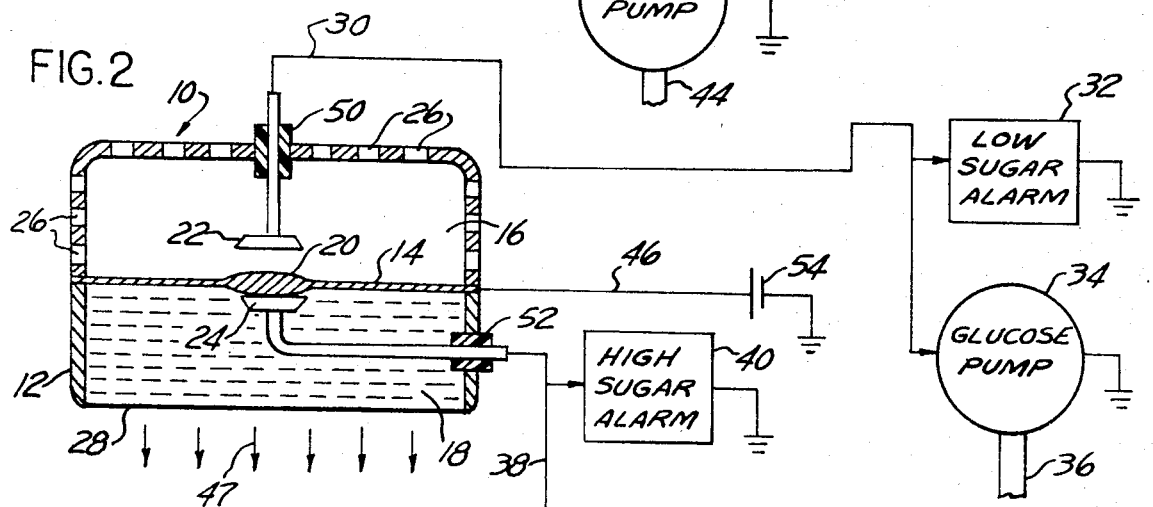
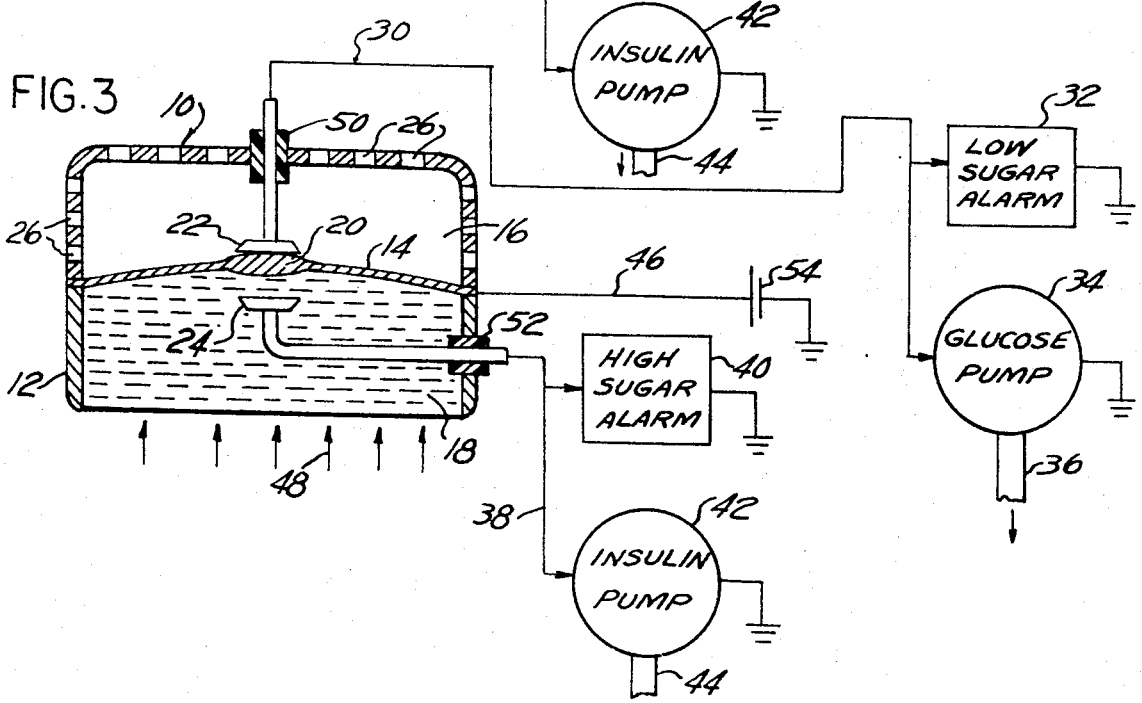

BLOOD SUGAR LEVEL SENSING AND
MONITORING TRANSDUCER

BACKGROUND OF THE INVENTION

The present invention relates to a blood sugar sensor and monitor, and more particularly to an implantable transducer capable of detecting variations in blood sugar level by detecting changes in blood osmotic pressure.

Among the therapeutic measures taken for controlling blood glucose concentration or values in patients subject to diabetes mellitus, insulin has been found particularly effective as a result of exerting a direct effect on glucose, protein and lipid metabolism. However, proper dosage of insulin injection is particularly critical as too high a dosage may cause hypoglycemia if too much insulin, or too little food, is taken by the patient. If hypoglycemia occurs, it must be treated through glucose administration.

In addition, control of a diabetic's blood sugar levels through, for example, once-a-day insulin injections presents the inconvenience of causing somewhat drastic rises and falls in blood sugar levels which, some diabetogists believe, could be responsible for the degeneration of blood vessels, resulting from excess blood glucose.

Insulin pump apparatus or insulin infusion pumps, have been recently developed for the treatment of hospitalized and ambulatory diabetics. The pump is connected through appropriate flexible conduits to subcutaneous needles or cannulae inserted in the abdomen, for example. Operation of the infusion pump is controlled by a microprocessor, according to a predetermined program, to inject an appropriate amount of insulin into the patient's bloodstream at appropriate intervals or, alternatively, to provide a constant insulin flow rate. An appropriate manual control is also often provided for delivering a pre-programmed dosage of insulin prior to meals for handling the blood sugar level increase following the ingestion of food.

Insulin infusion pumps have been miniaturized to the point that they are approximately of the size of a miniature radio receiver or pocket calculator, worn on a belt by ambulatory diabetics. Proper use of insulin infusion pumps requires adequate monitoring of the user's blood glucose levels, in order to avoid hypoglycemia and hyperglycemia. Monitoring of the blood glucose level permits to insure that the insulin delivery rate of the pump is neither excessive nor insufficient, and that the rate of injection of insulin is controlled as a function of the blood glucose level if such level can be determined in real time by an appropriate sensor or monitor. Unfortunately, no practical miniature blood glucose level sensing and monitoring transducer has, until the present, been developed that would permit automatic operation of a portable insulin infusion pump, without human intervention for monitoring a diabetic's blood glucose level.

Blood glucose level sensors or monitors presently available are of the chemical or of the electrolytic type. Whatever the type used they are generally complex, heavy and cumbersome, thus defeating the portability advantages of the miniaturized microprocessor controlled insulin infusion pumps. Furthermore, such sensors or monitors require that a second pair of cannulae be implanted in the patient with an appropriate flexible conduit network permitting blood to circulate through the sensor and be returned to the patient's bloodstream.

An ideal blood glucose level sensor or monitor capable of directly controlling the operation of an insulin infusion pump administrating an appropriate dosage of insulin when the blood sugar level reaches an unacceptable level, and, in addition, capable of remotely controlling a glucose infusion pump for administrating an appropriate dosage of glucose in the event that a patient's blood sugar level decreases below an acceptable level, should be preferably in the form of a relatively small transducer which could be easily implanted in the patient's bloodstream and which would be effective in operation and reliable over a long period of time, and safe in use.

The present invention provides such a sensor and monitor transducer which utilizes as principle of operation variations in blood osmostic pressure resulting from changes in blood sugar levels.

Blood osmostic pressure is a function primarily of concentration of sodium chloride, concentration of urea, and concentration of blood sugar or glucose. Under normal circumstances, the concentration of sodium chloride and the concentration of urea are constant, even in individuals affected with diabetes mellitus. The concentration of sodium chloride increases under unusual circumstances such as severe dehydration and decreases below normal also under unusual circumstances such as extreme overhydration. Concentration of urea also increases under unusual circumstances such as acute or chronic kidney failure. Absent such unusual circumstances, in a normal individual and in a diabetic individual, changes in osmostic blood pressure relate directly to rises and falls in blood glucose levels.

SUMMARY OF THE INVENTION

The present invention provides a blood glucose level sensor or monitor responsive to changes in osmostic pressure of the blood which in turn varies as a function of blood sugar or glucose concentration.

The principal object of the invention is to provide a blood glucose level sensor or monitor, in the form of a miniature transducer implantable in the bloodstream of a patient and adapted to either activate high blood sugar level and low blood sugar level alarms, or to operate infusion pumps for injection of either insulin or of a glucose solution, as required, or both.

These and other objects of the present invention will become apparent to those skilled in the art when the following description of the best mode contemplated at the present for practicing the invention is read in conjunction with the accompanying drawing wherein:

BRIEF DESCRIPTION OF THE DRAWING

FIG. 1 is a schematic representation of a therapeutic blood high glucose level alarm cum insulin pump and blood low glucose level alarm cum glucose pump system, incorporating an osmostic transducer for blood glucose sensing and monitoring according to the present invention;

FIG. 2 is a schematic view similar to FIG. 1 but illustrating the operation of the invention in the case of high blood glucose level; and FIG. 3 is a view similar to FIGS. 1 and 2 but illustrating the operation of the invention in the case of low blood glucose level.

DETAILED DESCRIPTION OF THE PREFERRED EMBODIMENT

Referring to the drawing and more particularly to FIG. 1, there is illustrated schematically a blood glucose level monitor or sensor in the form of a transducer 10 of relatively small size, such as to be adapted to be surgically implanted in the bloodstream of a person. The transducer 10 is formed of an enclosure or housing 12, a few millimeters in diameter and length, made of appropriate substantially non-corrosive and non-oxidizable inert material such as a plastic, preferably a silicone plastic or a metal such as silver or stainless steel, for example, made of two portions separated by a flexible impermeable diaphragm 14 such as to divide the housing 12 in two separate chambers 16 and 18. The impermeable flexible diaphragm 14 which may be made of flexible and elastic plastic, such as a silicone plastic or of a thin metallic plate preferably coated with a thin film of silicone and provided with concentric annular undulations, not shown, such that the flexible diaphragm 14 is capable of bowing toward the chamber 16 or toward the chamber 18, according to the pressure differential between the two chambers. The flexible diaphragm 14 is provided with an electrical contact 20 engageable with a fixed electrical contact 22 disposed in the chamber 16 or with a fixed electrical contact 24 disposed in the chamber 18, according to the direction in which the diaphragm 14 is caused to bulge. The chamber 16 is provided with perforated walls, as shown at 26, such that when the housing 12 of the transducer 10 is implanted in the bloodstream of a person, blood is free to circulate through the chamber 16, but is prevented to penetrate into the chamber 18 by the impermeable diaphragm 14.

The chamber 18 has imperforate walls, except where it is provided with a semi-permeable membrane 28. The semi-permeable membrane 28 may be made of any convenient semi-permeable material such as a film of cellulose acetate, for example, of a pore size impermeable to glucose molecules. The chamber 18 is filled with a standard osmotic solution, namely a standard aqueous solution or serum solution of glucose at normal concentration, for example of 280–300 milliequivalent per liter. The outer surface of the semi-permeable membrane 28 is directly in contact with the blood flowing through the bloodstream of the person in whom the housing transducer 12 is implanted. As long as the blood glucose concentration of the person is normal, that is corresponding to the glucose concentration or level in the standard solution in the chamber 18, the osmotic pressure of the standard solution and of the person's blood being in equilibrium, the diaphragm 14 remains in its neutral pre-designed position wherein its electrical contact 20 is disengaged from both the fixed electrical contact 22 in the chamber 16 and the fixed electrical contact 24 in the chamber 18. The electrical contact 22 in the chamber 16 is connected through an electrical conductor 30 to a low blood sugar alarm 32 and to an electric motor driving a glucose pump 34 having an outlet 36 connected, by an appropriate flexible hose and a needle or cannula, not shown, to the patient's bloodstream. The fixed electrical contact 24 in the chamber 18 is connected through an electrical conductor 38 to a high blood sugar alarm 40 and to the drive motor of an insulin pump 42 having an outlet 44 similarly connected to the patient's bloodstream. It will be readily appreciated that the movable electrical contact 20 on the deformable diaphragm 14, via an electrical conductor 46 closes the circuit of the low sugar alarm 32 and glucose pump 34 when engaged with the fixed electrical contact 22 in the chamber 16 or, alternatively, closes the circuit of the high blood sugar alarm 40 and insulin pump 42 when engaged with the fixed electrical contact 24 in the chamber 18.

In the event that the patient's blood glucose level rises beyond an acceptable level, the osmotic pressure of the blood wetting the outer surface of the semi-permeable membrane 28 exceeds the osmostic pressure of the standard osmotic solution in the chamber 18. Fluid is transferred through the osmotic semi-permeable membrane 28 from the interior of the chamber 28 to the bloodstream, as represented arbitrarily by the arrows 47. As fluid has been drawn from the chamber 18, the volume of the chamber 18 is decreased, thus drawing the diaphragm 14 and causing it to bulge into the chamber 18, with the result that the electrical contact 20 on the diaphragm 14 engages the fixed electrical contact 24 in the chamber 18. The circuit through the electrical conductors 38 and 46 is thus closed, which activates the high blood sugar alarm 40 to give an indication that insulin must be administered to the patient or, in automatic systems, which activates the insulin pump 42 to inject an appropriate dosage of insulin through the pump outlet 44 into the patient's bloodstream or, in the alternative, activates both the high blood sugar alarm 40 and the insulin pump 42.

Conversely, and as schematically illustrated at FIG. 3, low blood sugar concentration lowers the blood osmostic pressure below that of the standard solution in the chamber 18, and through fluid passing through the semi-permeable membrane 28 from the person's bloodstream into the chamber 18, as arbitrarily represented by the arrows 48, the volume of the solution in the chamber 18 is increased, thus deflecting the flexible impermeable diaphragm 14, as illustrated, such as to place the electrical contact 20 on the diaphragm 14 in engagement with the fixed electrical contact 22 in the chamber 16. The circuit through the electrical conductors 30 and 46 is closed, thus activating the low sugar alarm 32 and/or the glucose pump 34. When the glucose pump 34 is activated, a glucose solution is fed through the outlet 36 of the glucose pump 34 into the patient's bloodstream.

It will be appreciated by those skilled in the art that in structure wherein the housing 12 of the transducer 10 is metallic, the fixed electrical contacts 22 and 24 are insulated from the housing 12 by appropriate dielectric collars, as shown at 50 and 52, and that the diaphragm 14, if metallic, is also insulated from the housing 12. In structure wherein the flexible deformable diaphragm 14 is made of dielectric material, such as silicone or rubber, the contact 20 carried by the diaphragm 14 is appropriately connected to the electrical conductor 46 by a thin electrical wire, not shown. The three electrical conductors 30, 38 and 46 are of very small gauge and can be capsulated with their individual insulation sleeves to form of a tiny cable, as they are part of an electrical circuit of very low voltage and current as provided by a source of electricity arbitrarily represented by a battery 54. The battery 54 and the peripheral equipment consisting of the alarm devices 32 and 40 and the pumps 34 and 42 are connected to the transducer 10 through the cable of the electrical conductors or wires 30, 38 and 48, and are operated through appropriate relays.

Having thus described the present invention by way of an example of structure well designed to accomplish the objects of the invention, modifications whereof will be apparent to those skilled in the art, what is claimed as new is as follows:

1. A blood glucose sensor and monitor transducer comprising an enclosure implantable in the bloodstream of a person, an imperforate impermeable flexible diaphragm disposed in said enclosure and separating said enclosure into a first chamber open to the bloodstream and a second chamber, an osmostic semi-permeable membrane separating said second chamber from the bloodstream, a first electrical contact mounted on said diaphragm, a second electrical contact fixedly mounted in said first chamber and a third electrical contact fixedly mounted in said second chamber, and an osmostic solution filling said second chamber, whereby variations in glucose level of the blood in the bloodstream causing variations in osmotic pressure of the blood causes transfer of liquid fluid from and into said second chamber through said semi-permeable membrane deflecting said flexible diaphragm in one direction and in an opposite direction causing said first electrical contact on said flexible diaphragm to engage said second or third fixed electrical contact according to the direction of deflexion of said flexible diaphragm.

2. The transducer of claim 1 wherein a low blood sugar level alarm is connected across said first and second electrical contact.

3. The transducer of claim 1 wherein a high blood sugar level alarm is connected across said first and third electrical contacts.

4. The transducer of claim 1 wherein a pump is connected across said first and second electrical contacts, said pump being adapted to inject glucose into the bloodstream.

5. The transducer of claim 2 wherein a pump is connected across said first and second electrical contacts, said pump being adapted to inject glucose into the bloodstream.

6. The transducer of claim 1 wherein a pump is connected across said first and third electrical contacts, said pump being adapted to inject insulin into the bloodstream.

7. The transducer of claim 3 wherein a pump is connected between said first and third electrical contacts, said pump being adapted to inject insulin into the bloodstream.

8. The transducer of claim 4 wherein a pump is connected across said first and third electrical contacts, said pump being adapted to inject insulin into the bloodstream.

9. The transducer of claim 5 wherein a pump is connected across said first and third electrical contacts, said pump being adapted to inject insulin into the bloodstream.

* * * * *

UNITED STATES PATENT AND TRADEMARK OFFICE
CERTIFICATE OF CORRECTION

PATENT NO. : 4,538,616
DATED : 9/3/85
INVENTOR(S) : Robert Rogoff

It is certified that error appears in the above-identified patent and that said Letters Patent are hereby corrected as shown below:

Correct the spelling of "osmotic" throughout the specification and claims, namely at lines 5 and 6 of the Abstract, at column 2, lines 18, 21, 33, 39 and 60, Col.3, at line 51, Col. 4, at lines 9, 11, 12, 31-32, and at claim 1 at lines 6, 11-12 and 14.

Col. 3, line 20, change "and" to --is--

Col. 4, line 14, change "chamber 28" to --chamber 18--

Col. 4, line 61, cancel "of",

Col. 4, line 68, change "48" to --46--.

Signed and Sealed this

Twenty-eighth Day of January 1986

[SEAL]

Attest:

DONALD J. QUIGG

Attesting Officer

Commissioner of Patents and Trademarks